US009738942B2

(12) United States Patent
Dai et al.

(10) Patent No.: US 9,738,942 B2
(45) Date of Patent: Aug. 22, 2017

(54) USE OF LET-7G TO DOWN REGULATE NS5B GENE, CORE PROTEIN AND VIRAL LOAD OF HEPATITIS C VIRUS

(71) Applicant: KAOHSIUNG MEDICAL UNIVERSITY, Kaohsiung (TW)

(72) Inventors: Chia-Yen Dai, Kaohsiung (TW); Ming-Lung Yu, Kaohsiung (TW); Wan-Long Chuang, Kaohsiung (TW); Wen-Wen Chou, Kaohsiung (TW)

(73) Assignee: KAOHSIUNG MEDICAL UNIVERSITY, Kaohsiung (TW)

( * ) Notice: Subject to any disclaimer, the term of this patent is extended or adjusted under 35 U.S.C. 154(b) by 0 days.

(21) Appl. No.: 15/027,692

(22) PCT Filed: Mar. 31, 2014

(86) PCT No.: PCT/US2014/032329
§ 371 (c)(1),
(2) Date: Apr. 6, 2016

(87) PCT Pub. No.: WO2015/053813
PCT Pub. Date: Apr. 16, 2015

(65) Prior Publication Data

US 2016/0251734 A1 Sep. 1, 2016

(30) Foreign Application Priority Data

Oct. 11, 2013 (TW) ............................ 102136708 A

(51) Int. Cl.

| | |
|---|---|
| ***A61K 31/7105*** | (2006.01) |
| ***G01N 33/576*** | (2006.01) |
| ***G01N 33/50*** | (2006.01) |
| ***A61K 38/21*** | (2006.01) |
| ***C12Q 1/68*** | (2006.01) |
| ***C12Q 1/70*** | (2006.01) |
| ***A61K 31/7056*** | (2006.01) |

(52) U.S. Cl.
CPC .......... *C12Q 1/707* (2013.01); *A61K 31/7056* (2013.01); *A61K 38/21* (2013.01); *G01N 33/5767* (2013.01); *C12Q 2600/106* (2013.01); *C12Q 2600/178* (2013.01)

(58) Field of Classification Search
None
See application file for complete search history.

(56) References Cited

PUBLICATIONS

Murakami et al. BMC Medical Genomics 2010, vol. 3, pp. 48-60.*
Kenneth J. Livak and Thomas D. Schmittgen, "Analysis of relative gene expression data using real-time quantitative PCR and the 2-ΔΔCT method." methods 25 (2001): 402-408.
Schmittgen, Thomas D., et al. "Real-time PCR quantification of precursor and mature microRNA." Methods 44.1 (2008): 31-38. doi:10.1016/j.ymeth.2007.09.006.
International search reports for PCT/US2014/032329, dated Aug. 26, 2014.

* cited by examiner

*Primary Examiner* — Tracy Vivlemore
(74) *Attorney, Agent, or Firm* — Hannah M. Tien

(57) ABSTRACT

A method for evaluating the therapeutic efficacy of interferon (IFN)/ribavirin (RBV) for hepatitis C is disclosed. The method includes the steps of providing a specimen; mixing the specimen, a primer of a miRNA Let-7g and a poly-chain reaction (PCR) reagent together; and evaluating the efficacy of IFN/RBV on inhibiting a hepatitis C virus according to the expressing level of the miRNA Let-7g in the specimen detected by the PCR reagent.

3 Claims, 18 Drawing Sheets

```
Let-7g      3'  u u G A C A - U G U U U G A U G G A G u  5'
                    | | | |   |   : | | | | : : | | :
HCV 5'UTR   5'  c c C T G T G A G G A A C T G T C T T c  3'
```

Fig. 1(A)

USE OF LET-7G TO DOWN REGULATE NS5B GENE, CORE PROTEIN AND VIRAL LOAD OF HEPATITIS C VIRUS

CROSS-REFERENCE TO RELATED APPLICATION AND CLAIM OF PRIORITY

This application claims the benefit of Taiwan of Taiwan Patent Application No. 102136708, filed on Oct. 11, 2013, at the Taiwan Intellectual Property Office, the disclosures of which are incorporated herein in their entirely by reference. This application is the national stage of PCT International Application No. PCT/US2014/032329 filed on Mar. 31, 2014. The sequence listing text file, file name 2609-KMU-US_SEQ created Apr. 6, 2016, file size 1237 bytes, is incorporated herein by reference in its entirety.

FIELD OF THE INVENTION

The present invention relates to the use of Let-7g, and more particularly to the use of Let-7g to down regulate the NS5B gene, core protein and viral load of the hepatitis C virus.

BACKGROUND OF THE INVENTION

There are 1.3 to 1.7 billion people in the world (about 2%-3% of the world's population) chronically infected with the hepatitis C virus (HCV). Hepatitis C is one of the major etiologies of liver disease and liver cancer. In developed countries, the antibody of the hepatitis C virus occurs in a range of 1%-2%. In some areas with a high prevalence of hepatitis C, the occurrence can be above 20%. A mixture of therapies with long efficacy interferon (say IFN-α) and ribavirin are used in current clinical treatments. In addition, a treatment for patients with sustained virologic response (SVR) of chronic hepatitis C is done clinically in general according to the genotype of the virus or host and a combination of IFN/ribavirin. The ratio of this treatment could reach 50%-85%. About 3%-4% of the population suffers from hepatitis C in our country. However, the therapeutic efficacy of treatment using the combination of IFN/ribavirin is only about 70%; not only does the treatment course continue for 6-12 months, but it is also accompanied by substantial side effects, and the patient's daily life is severely affected.

Because the expression level of miRNA is associated with diseases, quantitative analysis of miRNA can be a means to reveal the mechanism of diseases as a target of new drug development. In previous studies, it was found that miR-122, one of the micro ribonucleic acids in a vertebrate, is combined with two positions in the genome of the hepatitis C virus, which strongly facilitates the replication of the virus. Hence, if one realizes the specificity of the genome of the hepatitis C virus to combine with the miR-122 and block the specificity for replication of the virus, it might be possible to relieve the hepatitis C virus infection. Currently a pharmaceutical manufacturer has developed a drug to inhibit the activity of miR-122, which has proceeded to the clinical trial phase.

Some studies suggest that beta-interferons (IFN-β) up regulate certain miRNAs, for example miR-196, miR-296, miR-351, miR-431 and miR-448, and can be combined with predicting sequences in the genome of the hepatitis C virus to reduce its replication and infection. In addition, it was found that expression levels in the members of a Let-7 family are reduced, including lung cancer, hepatocellular carcinoma (HCC), hepatocellular carcinoma and metastatic liver cancer.

Cheng J C et al., Cell Mol Life Sci. 2012 August; 69 (15): 2621-33 once mentioned that Let-7b, which belongs to a family member of the miRNA Let-7, can reduce the expression level of the NS5A gene and a core protein of the hepatitis C virus, and referred to a decreasing expression level of the Let-7b. Combined interferon/ribavirin may have a synergistic inhibitory effect on the luciferase activity in the virus. However, Cheng is silent about whether the Let-7b has effects on interferon stimulated genes (ISGs). In addition, these results are from in vitro experiments, and there are no experiments for practical examples in vivo as evidence.

SUMMARY OF THE INVENTION

In the present invention, it is proposed that Let-7g be combined with one position in the genome of the hepatitis C virus (HCV) to inhibit the replication of the virus. In the cell model of the HCV infection, Let-7g not only controls the expression level of a core protein, but also reduces the viral load secreted by the HCV. In addition, it was found that compared to patients with SVR, there is a significant drop of Let-7g in the serum or the liver tissue in patients with non-SVR before the treatment. That is, both of the expression levels of Let-7g in patients with non-SVR are lower, so Let-7g can be used to predict the therapeutic efficacy of interferon. Let-7g may be involved in the pathogenesis of chronic hepatitis C virus infection and the response to treatments. Let-7g has the potential to be developed as a target drug for HCV. Let-7g may serve as a therapeutic drug and additively cooperate with interferon/ribavirin.

In accordance with an aspect of the present invention, a method for evaluating the therapeutic efficacy of interferon (IFN)/ribavirin (RBV) for hepatitis C is disclosed. The method includes the steps of providing a specimen; mixing the specimen, a primer of a miRNA Let-7g and a poly-chain reaction (PCR) reagent together; and evaluating the efficacy of IFN/RBV on inhibiting the hepatitis C virus according to an expressing level of the miRNA Let-7g in the specimen detected by the PCR reagent.

In accordance with another aspect of the present invention, a kit for evaluating the therapeutic efficacy of interferon (IFN)/ribavirin (RBV) for hepatitis C is disclosed. The kit includes a primer of miRNA Let-7g for mixing with a specimen; and a poly-chain reaction reagent for mixing with the primers of the miRNA Let-7g and the specimen, wherein the therapeutic efficacy of IFN/RBV is evaluated according to an expressing level of the miRNA Let-7g.

In accordance with a further aspect of the present invention, a method for regulating an activity of a hepatitis C virus (HCV) is disclosed. The method includes a step of down regulating at least one of an expressing level of a NS5B gene, an expressing level of a core protein and a viral load of HCV using miRNA Let-7g.

The above objectives and advantages of the present invention will become more readily apparent to those ordinarily skilled in the art after reviewing the following detailed descriptions and accompanying drawings, in which:

BRIEF DESCRIPTION OF THE DRAWINGS

FIGS. 1(A)-1(C) are diagrams indicating relevant experiments showing that a Let-7g may be combined with a 5'untranslated region of a genome of the HCV in a Ava.5 cell;

DETAILED DESCRIPTION OF THE PREFERRED EMBODIMENTS

The present invention will now be described more specifically with reference to the following embodiments. It is to be noted that the following descriptions of preferred embodiments of this invention are presented herein for the purposes of illustration and description only; it is not intended to be exhaustive or to be limited to the precise form disclosed.

The present invention makes a detailed description of the embodiments and the relevant experimental results below.

Embodiment 1

The present invention uses the sequence of Ava.5 cells (no. AJ242654.1 in the gene bank) to make predictions. It is found that the miRNA Let-7g may be combined with position bearing nucleotides of No. 43-65 in the 5'untranslated region (5'UTR) of a genome of the HCV (please refer to FIG. 1(A)).

Embodiment 2

Figure 1B:
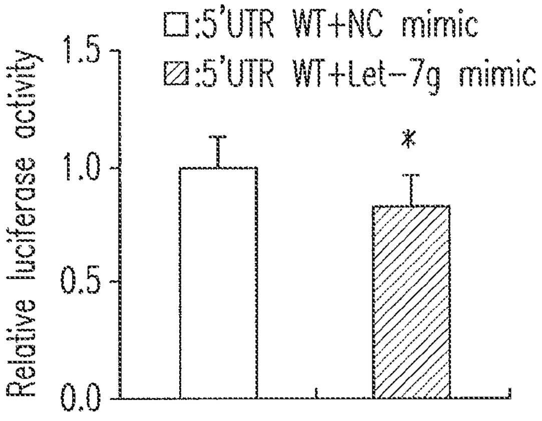
Figure 1C:
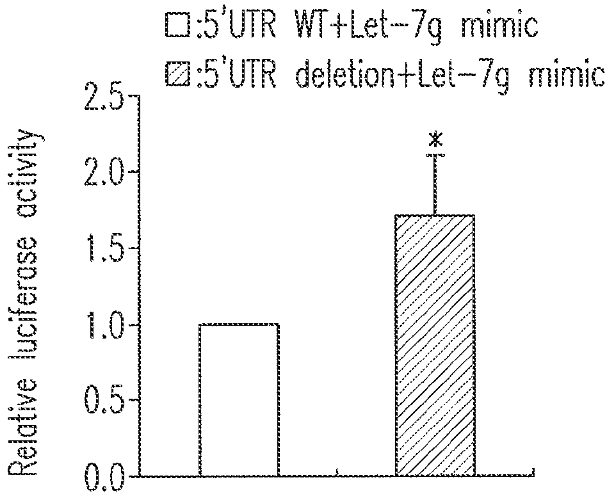

For a further confirmation, the present invention constructs a Let-7g luciferase reporter plasmid capable of direct combination (hepatitis C virus 5'UTR-WT), and a Let-7g luciferase reporter plasmid lacking Let-7g combining sequences (hepatitis C virus 5'UTR-DEL). In FIG. 1(B), a Let-7g mimic (■) or a negative control (NC) mimic, as well as a luciferase reporter plasmid for a hepatitis C virus 5'UTR-WT are transgened into Ava.5 cells carrying the genome of the hepatitis C virus. In FIG. 1(C), a Let-7g mimic along with a luciferase reporter plasmid of a hepatitis C virus 5'UTR-WT (□) or a hepatitis C virus 5'UTR-DEL (■) together are transgened into Ava.5 cells carrying the genome of the hepatitis C virus. 48 hours later, the activity values of luciferases in the Ava cell values are determined, and a green luciferase protein (GFP) served as an internal control. The data in this embodiment was sampled from three trials and represented as the average±standard deviation of *P<0.05.

The experimental results show that once transfecting a plasmid containing a hepatitis C virus 5'UTR-WT for the Let-7g mimic, compared to the negative control (NC), it can be seen that the relative luciferase activity in the cells was reduced (please refer to FIG. 1(B)).

However, once transfecting a plasmid containing the Let-7g mimic and lacking Let-7g combining sequences (hepatitis C virus 5'UTR-DEL), compared to a plasmid containing a hepatitis C virus 5'UTR-WT for the Let-7g mimic, it can be seen that the relative luciferase activity increased (please refer to FIG. 1(C)). This illustrates that the Let-7g indeed directly binds to the 5'untranslated region of the HCV. Accordingly, the present invention confirmed that there is a combining sequence for Let-7g in the 5'UTR of the HCV.

Embodiment 3

Figure 2A:
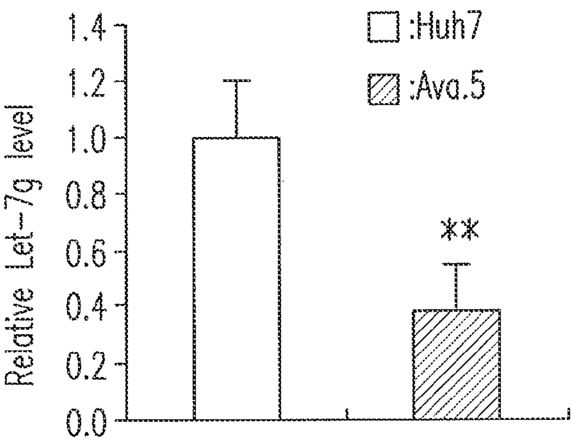
FIGS. 2(A)-2(B) are diagrams indicating expression levels of Let-7g in a Huh7 cell line, a Huh7.5.1 cell line, Ava.5 replicon cells and JFHI infected cells.

In order to explore the relationship between Let-7g and an infection of HCV, the present invention detects expression levels of the Let-7g in a virus replicon and infected cells. In FIG. 2(A), the Huh7 and Ava.5 cells were cultured for 72 hours, and then the RNA was separated. In FIG. 2 (B), Huh7.5.1 cells were cultured for 24 hours and then cell-culture derived HCV infected cells JFH1 HCVcc were added, and then its RNA was separated 72 hours after the infection. We used quantitative real time PCR to detect the expression levels of the Let-7g, and used snU6B as an internal control. In addition, a Let-7g mimic or a negative control mimic (NC) was transfected into Ava.5 cells (please refer to FIG. 2 (C)) or infected cells JFH1 (please refer to FIG. 2 (D)), and its RNA was separated 72 hours after the infection. After that, we used quantitative real time PCR to detect expression levels of the NS5B protein of the HCV, and used glyceraldehyde-3-phosphate dehydrogenase (GAPDH) as an internal control, wherein each horizontal axis represents the concentration unit in nM. The data in this embodiment was sampled from three trials represented as the average±standard deviation of *P<0.05.

Figure 2B:
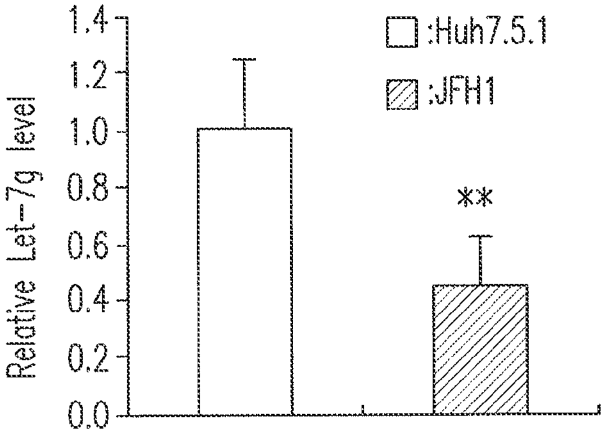
Figure 2C:
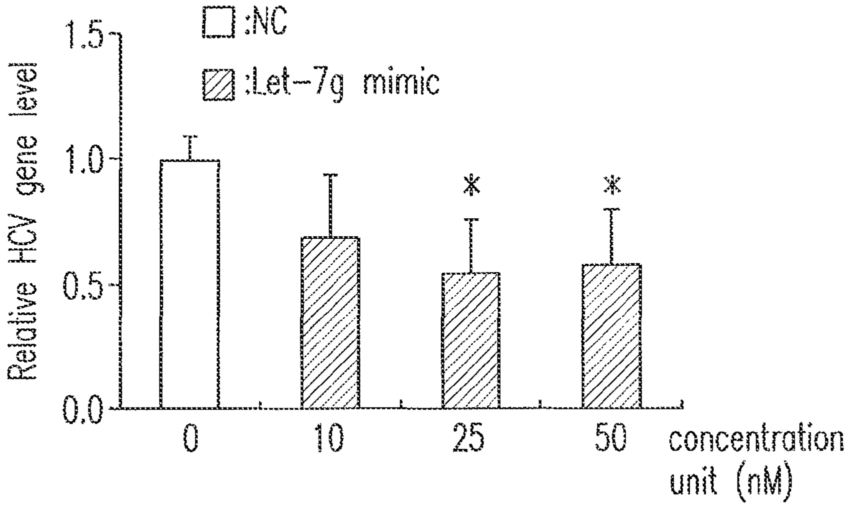
FIG. 2(C) is a diagram indicating expression levels of HCV in Ava.5 cells after a negative control mimic (NC) or a Let-7g mimic is transfected into Ava.5 cells.
Figure 2D:
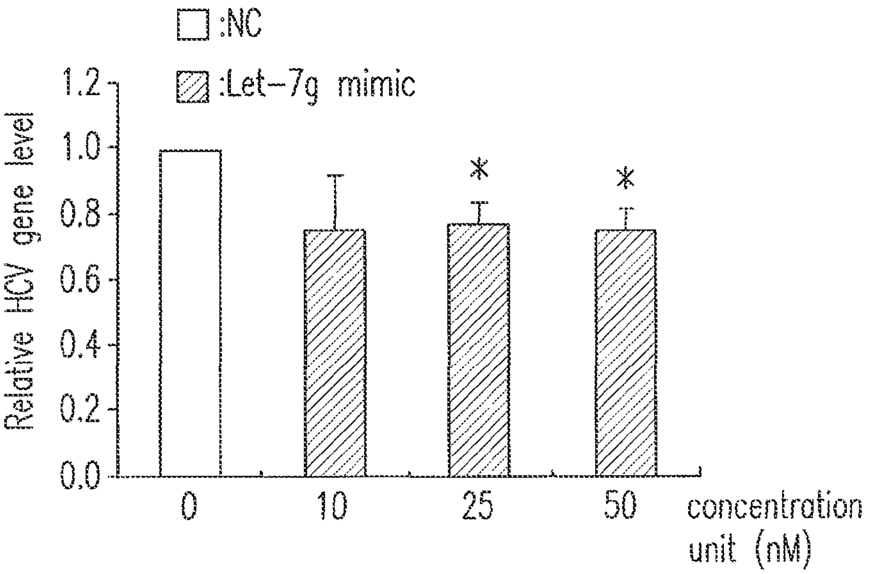
FIG. 2(D) is a diagram indicating expression levels of HCV in JFHI cells after a negative control mimic (NC) or a Let-7g mimic is transfected into JFHI cells.

It is found in the present invention that for the cells carrying the genome of the HCV (Ava.5) and those infected by the HCV (JFH), expression levels of Let-7g were significantly reduced (please refer to FIG. 2(A) and FIG. 2(B)). After the Let-7g mimic was transfected, the HCV gene levels of Ava.5 and JFH, infected cells, were reduced. That is, the Let-7g mimic down regulated the NS5B gene. It can be further deduced that expression levels of the Let-7g in the cells carrying the genome of HCV or those infected with the HCV can be similarly reduced (please refer to FIG. 2(C) and FIG. 2 (D)).

Embodiment 4

In order to clarify the role of the Let-7g in the HCV infection, the present invention processed Let-7g in a cell model infected with HCV JFH1 in vitro, and used the cells transfected with a miR-122 inhibitor as a positive control.

Figure 3A:
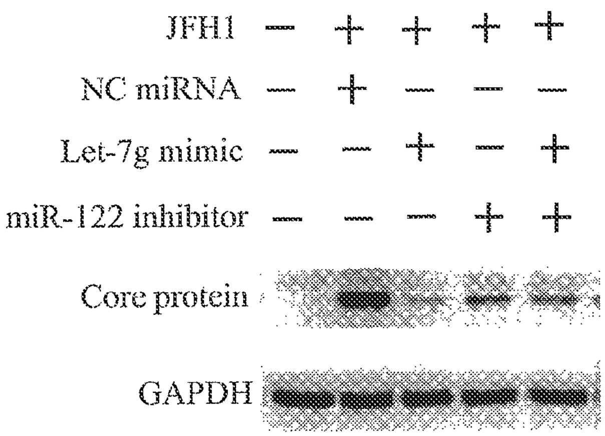
FIGS. 3(A)-3(D) are diagrams indicating experiments of a Let-7g in a cell model infected by HCV JFH1 in vitro, wherein a cell transfected by a miR-122 inhibitor served as a positive control.
Figure 3B:
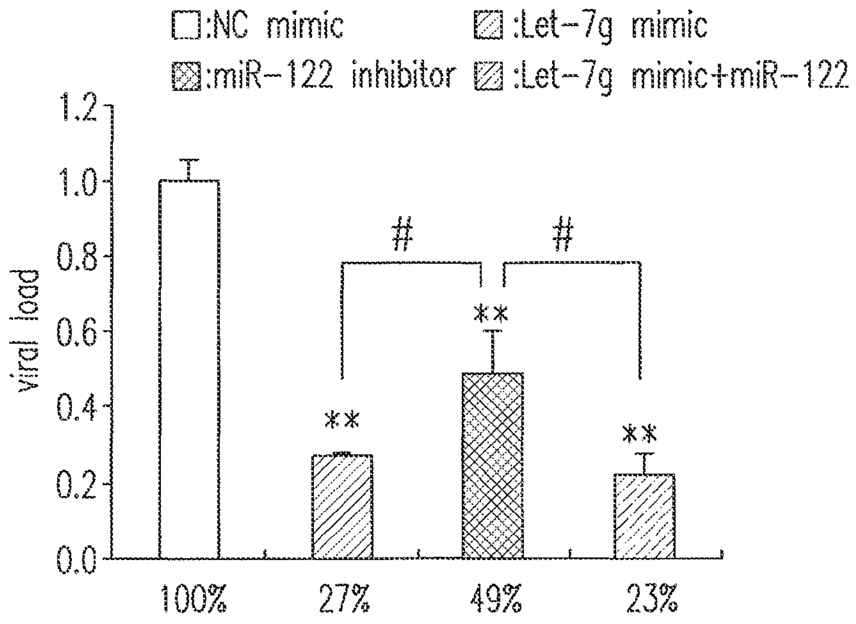

In this embodiment, a Huh7.5.1 cell line was cultured for 24 hours, and subsequently transfected with a Let-7g mimic, a miR-122 inhibitor or a negative control. 24 hours after the transfection, the cells were infected with JFH1 HCVcc. And 72 hours after the infection, interferon (100 IU/ml) or ribavirin (40 μM) were used to process the cells for 24 hours. And, 96 hours after the infection, supernatants were collected and the proteins were separated. In FIG. 3(A) and FIG. 3(*c*), a core protein of the HCV was analyzed using the Western Blot technique. In FIG. 3(B) and FIG. 3(D), the RNA of the HCV from the supernatants in the cell culture was analyzed using the Abbott quantitative Real Time Polymerase Chain Reaction (RT-PCR). The data in this embodiment was sampled from three trials represented as the average±standard deviation with **P<0.005, #P<0.05 and ##P<0.005.

The experimental results indicate that the Let-7g mimic and miR-122 inhibitor can both reduce the core protein of the HCV, representing down regulating the core protein (please refer to FIG. 3(A)).

In FIG. 3(B), the Let-7g mimic reduces the viral load of the virus infected cells by HCV JFH1 in vitro, accounting for about 73% (p<0.0005).

Figure 3C:
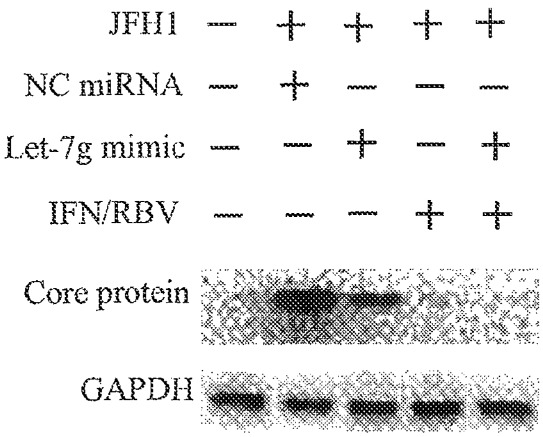
Figure 3D:
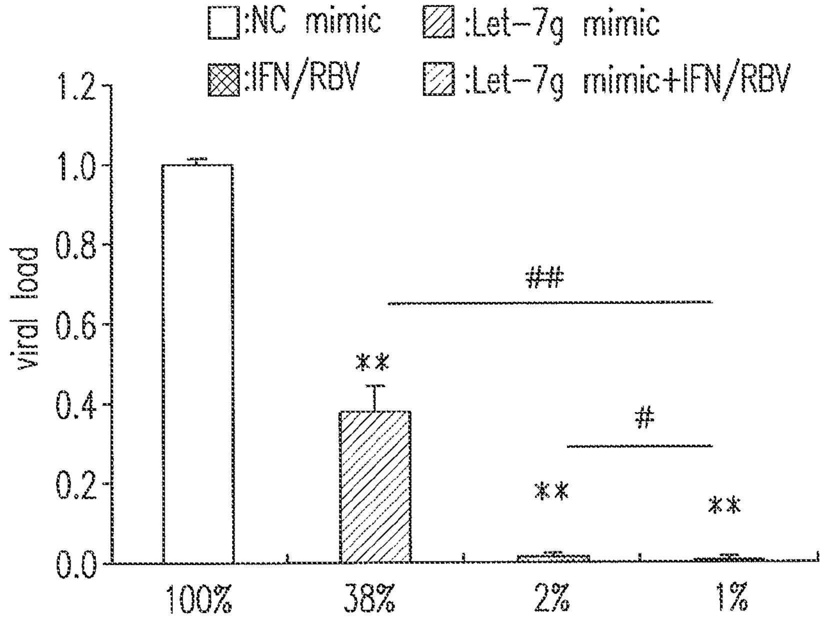

The Let-7g mimic and IFN/RBV can both reduce the expression of the core protein of the HCV (please refer to FIG. 3(C)).

The Let-7g mimic cooperating with IFN/RBV lowers the viral load of supernatants in virus infected cells JFH1, accounting for about 99% (p<0.0004). Let-7g reduces the infectivity of HCVcc, which means it down regulates the viral load (Please refer to FIG. 3(D)).

Embodiment 5

Figure 4A:
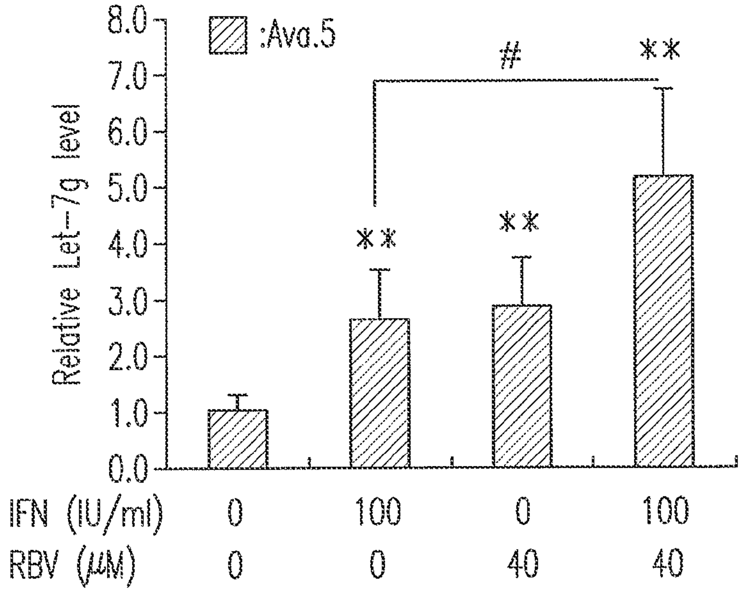
FIGS. 4(A)-4(F) are diagrams indicating relevant experimental results showing whether there is a additive effect among Let-7g and IFN/ribavirin.
Figure 4B:
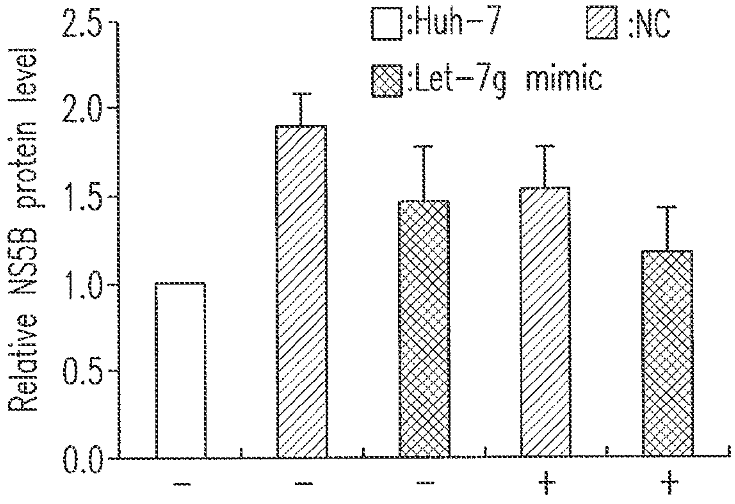
Figure 4C:
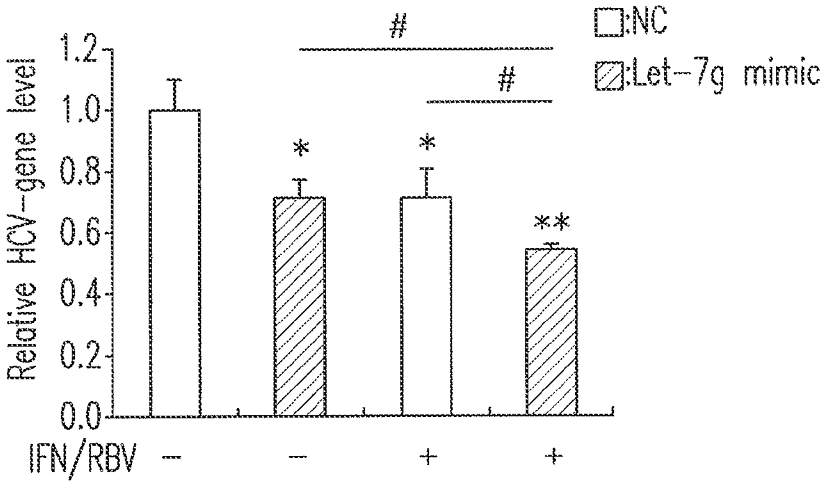
Figure 4D:
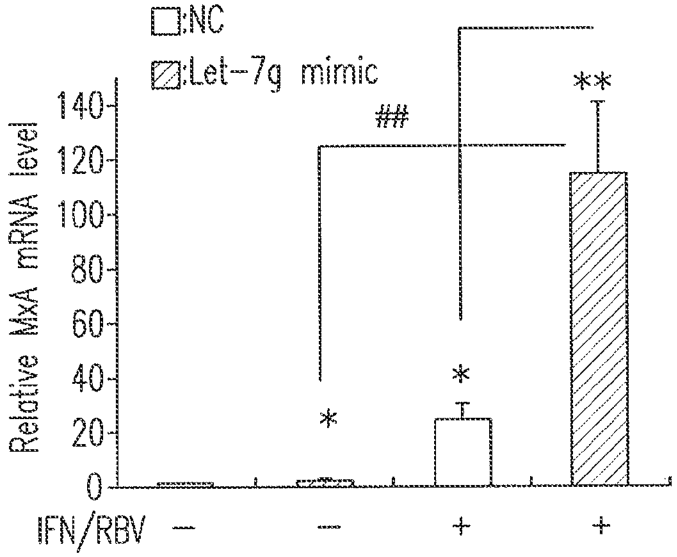
Figure 4E:
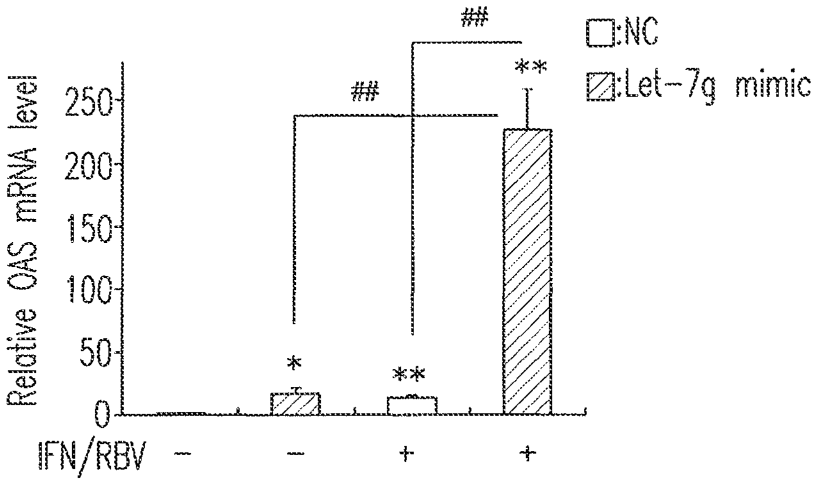
Figure 4F:
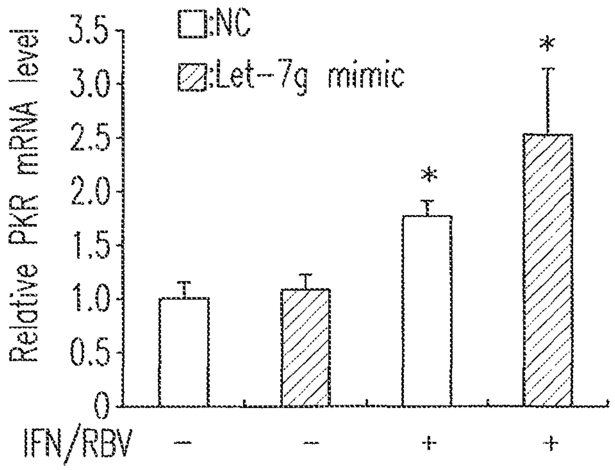

However, a mixed therapy consisting of long efficacy interferon (IFN-α) and ribavirin is often used in current clinical treatments. In FIG. 4(A), after Ava.5 cells were cultured for 24 hours, interferon (100 IU/ml) or ribavirin (40 μM) was used to process cells. 24 hours later, the RNA was separated. Quantitative real time PCR was used to detect expression levels of the HCV gene, and snU6B was used as an internal control. In FIGS. 4(C)-FIG. 4(F), Let-7g or a negative control mimic (NC) transfects Ava.5 cells, and the RNA was separated 72 hours after the infection. Quantitative real time PCR was used to detect expression levels of the NS5B protein of the HCV, and the level of GAPDH was used as an internal control. Quantitative real time PCR was used for detecting expression levels of the HCV gene, a myxovirus resistance protein A (MxA), a 2'-5' oligoadenylate synthetase (OAS) and a protein kinase R (PKR). GAPDH was used as an internal control as well. In FIG. 4(B), Western Blot was used to detect the expression of the NS5B protein in the HCV replicon cells. The relative level of the NS5B protein was quantized using Quantity One 1-D Analysis Software. The data in this embodiment was sampled from three trials represented as the average±standard deviation with *P<0.05, **P<0.05, #P<0.05.

Experimental results show that IFNα-2a cooperating with RBV can increase levels of the Let-7g (please refer to the relative Let-7g level in FIG. 4(A)).

Ava.5 cells were transfected by the Let-7g and then treated with IFN/RBV. It is possible to reduce the expression levels of the HCV gene and NS5B protein (please refer to FIG. 4(B) and FIG. 4(C)).

The present invention pointed out that type I and type II interferons up regulated Interferon-Stimulated Genes (ISGs), such as protein kinase R (PKR), 2'-5' oligoadenylate synthetase (OAS) and myxovirus resistance protein A (MxA), which are important factors for any anti-virus. Experimental results show that transfecting the Let-7g mimic alone induced the expression of MxA gene about 2 fold (please refer to FIG. 4(D)) and the OAS gene about 17 fold (please refer to FIG. 4 (E)), but did not affect the gene expression in PKR (please refer to FIG. 4(F)). The present invention further checked whether the Let-7g mimic cooperating with IFN/RBV impacts the additive effect among these interferon-stimulated genes. Data show that the Let-7g mimic cooperating with IFN/RBV induced the expression of MxA gene about 110 fold and the OAS gene about 226 fold (please refer to FIG. 4(D)-FIG. 4(E)). It can be seen that there was a additively induced effect between the Let-7g mimic and IFN/RBV. The antivirus effect of the Let-7g exactly depended on the IFN pathway.

Embodiment 6

To determine whether Let-7g could predict treatment response, serum Let-7g levels were determined in patients with SVR and non-SVR. Patients and clinical samples Eighteen patients with biopsy-proven chronic hepatitis C (CHC) from HCV genotype 1 infection and 17 controls with biopsy-proven non-alcoholic fatty liver disease (NAFLD) were included for the study of the liver tissue. All patients were treated with 48 weeks of pegylated IFN (PEG-IFN)/RBV with at least 80% adherence and 12 patients achieved an SVR (HCV RNA undetectable for 24 weeks after cessation of treatment) and 6 did not (non-SVR). Clinical serum data were obtained from 23 patients with SVR and 19 patients with non-SVR from HCV genotype 1 infection. Hepatic tissue and serum samples of CHC patients were collected before antiviral therapy. All of the NAFLD patients were seronegative for anti-HCV antibodies and hepatitis B surface antigen. The protocols involving human subjects were approved by the ethics committee at the Kaohsiung Medical University Hospital and were carried out according to the guidelines of the International Conference on Harmonization for Good Clinical Practice. All participants gave informed consent.

Statistical Analysis

Data of a continuous variable nature was expressed as the mean±standard deviation (SD). Unpaired t-tests were used to compare means between the two groups. Student's t test and the $X^2$ value were used to analyze patient characteristics. A multivariate logistic regression model was used to determine the factors associated with outcomes. All p values are two-sided, and a value of less than 0.05 was considered statistically significant. All statistical calculations were performed using JMP software (version 9).

Let-7g Level is Lower in Patients with Non-SVR

Our data showed that Let-7g was significantly decreased in the serum of patients with non-SVR when compared to SVR patients before antiviral therapy (please refer to Table 1, in which demonstrates factors associated with sustained virologic response (SVR) and non-SVR in serum). To determine the clinicopathological significance of Let-7g expression, liver tissue expression of Let-7g was analyzed by real-time PCR in patients with NAFLD and patients with chronic HCV infection with SVR and non-SVR before antiviral therapy. The Let-7g is significantly decreased in HCV-infected patients when compared to NAFLD patients (please refer to Table 2, in which demonstrates factors associated with non-alcoholic fatty liver disease (NAFLD) and HCV infection in liver tissue). Importantly, Let-7g expression in liver tissue was significantly lower in non-SVR patients when compared to SVR patients (please refer to Table 3, in which demonstrates factors associated with sustained virologic response (SVR) and non-SVR in liver tissue). These results indicate that decreased Let-7g expression levels correlate with treatment response.

TABLE 1

| | SVR (n = 23) | non-SVR (n = 19) | Univariate p value |
|---|---|---|---|
| Sex (M/F) | 14 (60.9)/9 (39.1) | 8 (42.1)/11 (57.9) | 0.226 |
| Age (years, mean (SD)) | 55.3 (8.8) | 55.0 (12.3) | 0.916 |
| BMI (kg/m$^2$, mean (SD)) | 24.3 (2.5) | 25.0 (3.5) | 0.449 |
| GPT (ALT) (IU/l, mean (SD)) | 103.7 (71.7) | 103.7 (56.0) | 0.999 |
| AC SUGAR (mean (SD)) | 109.5 (33.7) | 107.8 (30.3) | 0.888 |
| TG (mean (SD)) | 95.2 (46.6) | 108.3 (35.9) | 0.424 |
| CHOL (mean (SD)) | 161.8 (31.0) | 165.3 (44.6) | 0.807 |
| HDL-C (mean (SD)) | 37.0 (10.5) | 42.9 (14.1) | 0.210 |

TABLE 1-continued

| | SVR (n = 23) | non-SVR (n = 19) | Univariate p value |
|---|---|---|---|
| Let-7g levels | | | |
| $\log_{10}$ ($2^{-\Delta Ct(let7g\text{-}snU6B)}$ (mean (SD)) | 1.14 (0.40) | 0.67 (0.50) | 0.0015 |

* SD, standard deviation;
BMI, body mass index;
ALT, alanine aminotransferase;
TG, triglycerides;
CHOL, Cholesterol;
HDL-C, high-density lipoprotein cholesterol

TABLE 2

| | NAFLD (n = 17) | HCV (n = 18) | Univariate p value | Multivariate p value |
|---|---|---|---|---|
| Sex (M/F) | 7/10 | 10/8 | 0.3949 | |
| Age (years, mean (SD)) | 30.88 (11.24) | 48.28 (10.65) | <0.0001 | 0.0004 |
| BMI (kg/m$^2$, mean (SD) | 38.11 (6.53) | 23.32 (4.25) | <0.0001 | — |
| W/H ratio (mean (SD)) | 0.93 (0.12) | 0.86 (0.08) | 0.0784 | |
| CHOL (mean (SD)) | 188.56 (30.21) | 152.94 (44.11) | 0.0051 | 0.0031 |
| TG (mean (SD)) | 108.75 (52.99) | 111.56 (60.28) | 0.9878 | |
| HDL-C (mean (SD)) | 51.69 (18.91) | 41.82 (12.81) | 0.0784 | |
| GOT (AST) (IU/l, mean (SD)) | 26.00 (8.21) | 76.33 (47.24) | <0.0001 | — |
| GPT (ALT) (IU/l, mean (SD)) | 31.06 (17.45) | 115.72 (79.89) | <0.0001 | — |
| Let-7g levels | | | | |
| $2^{-\Delta Ct(Let\text{-}7g\text{-}RNU44)}$ (mean (SD)) | 2.24 (1.44) | 0.78 (0.71) | <0.0001 | <0.0001 |

* SD, standard deviation;
BMI, body mass index;
CHOL, Cholesterol;
TG, triglycerides;
HDL-C, high-density lipoprotein cholesterol;
AST, aspartate aminotransferase;
ALT, alanine aminotransferase;
"—" indicate the variable was excluded in step-wise logistic regression.

TABLE 3

| | SVR (n = 12) | non-SVR (n = 6) | Univariate p value | Multivariate p value |
|---|---|---|---|---|
| Sex (M/F) | 7/5 | 3/3 | 0.7373 | |
| Age (years, mean (SD)) | 45.33 (11.02) | 54.17 (7.49) | 0.0650 | |
| BMI (kg/m$^2$, mean (SD) | 21.65 (4.05) | 26.66 (2.29) | 0.0042 | 0.0002 |
| W/H ratio (mean (SD)) | 0.84 (0.08) | 0.90 (0.07) | 0.1256 | |
| CHOL (mean (SD)) | 143.92 (38.75) | 171.00 (52.20) | 0.2959 | |
| TG (mean (SD)) | 96.92 (65.71) | 140.83 (36.22) | 0.0183 | 0.0225 |
| HDL-C (mean (SD)) | 39.51 (11.90) | 46.45 (14.43) | 0.4593 | |
| GOT (AST) (IU/l, mean (SD)) | 62.08 (34.37) | 104.83 (59.37) | 0.1032 | |
| GPT (ALT) (IU/l, mean (SD)) | 109.33 (86.46) | 128.50 (70.42) | 0.3550 | |
| Let-7g levels | | | | |
| $2^{-\Delta Ct(Let\text{-}7g\text{-}RNU44)}$ (mean (SD)) | 1.00 (0.78) | 0.32 (0.13) | 0.0208 | 0.0008 |

* SD, standard deviation;
BMI, body mass index;
CHOL, Cholesterol;
TG, triglycerides;
HDL-C, high-density lipoprotein cholesterol;
AST, aspartate aminotransferase;
ALT, alanine aminotransferase.

Embodiment 7

The present invention further explores ways of regulating the activity of Let-7g. FIGS. 5(A)-5(H) are mainly about whether an RNA-binding protein lin28 and a small interfering RNA for lin28 (lin28 siRNA) can regulate the expression of the Let-7g.

Figure 5A:
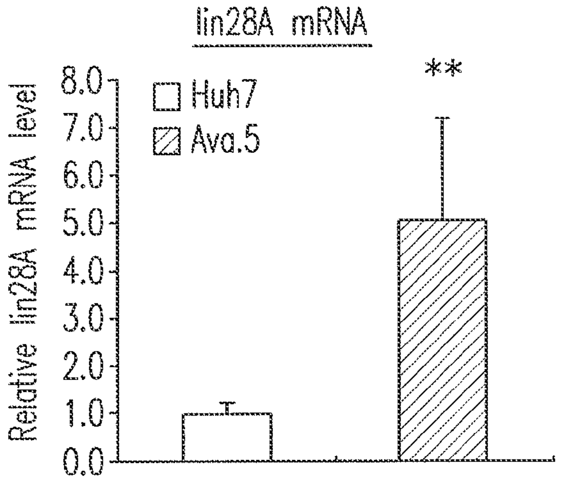
FIG. 5(A)-5(H) are diagrams indicating that both an RNA-binding protein lin28 and small interfering RNA (siRNA) can regulate the expression of Let-7g.
Figure 5B:
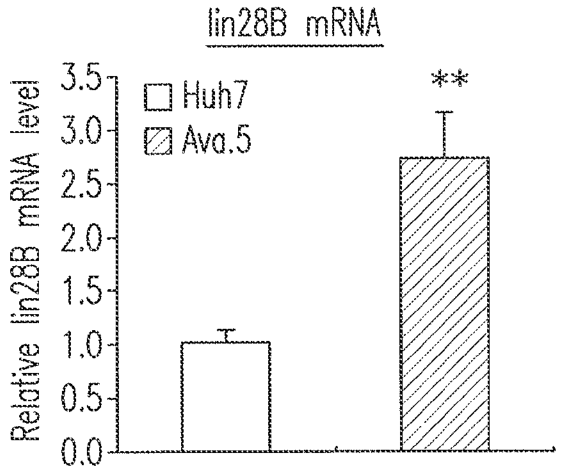

In FIGS. 5(A)-5(B), cell lines of Huh7 and Ava.5 were cultured for 72 hours, and then their RNA was separated.

Figure 5C:
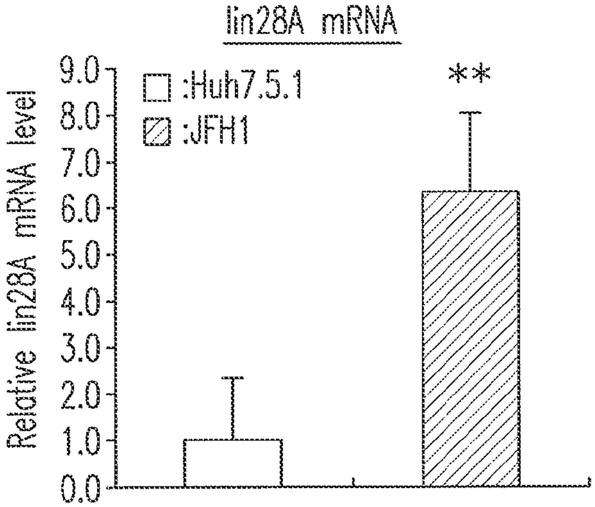
Figure 5D:
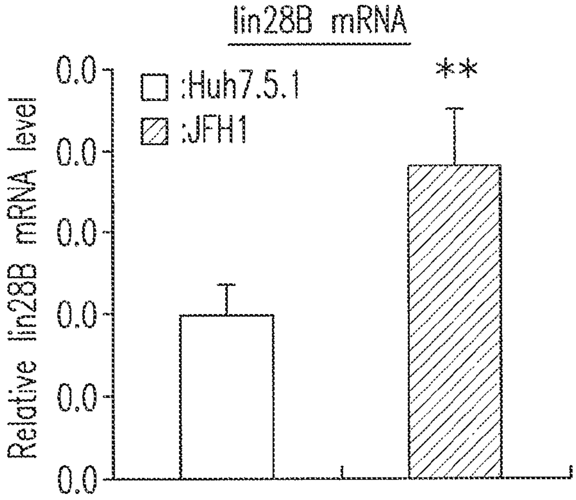

In FIGS. 5(C)-5(D), a Huh7.5.1 cell line with $1\times10^5$ cells was cultured for 24 hours and then infected with JFH1 HCVcc, and its RNA was separated 72 hours after the infection. Expression levels of lin28A or lin28B may be detected by RT-PCR.

Figure 5E:
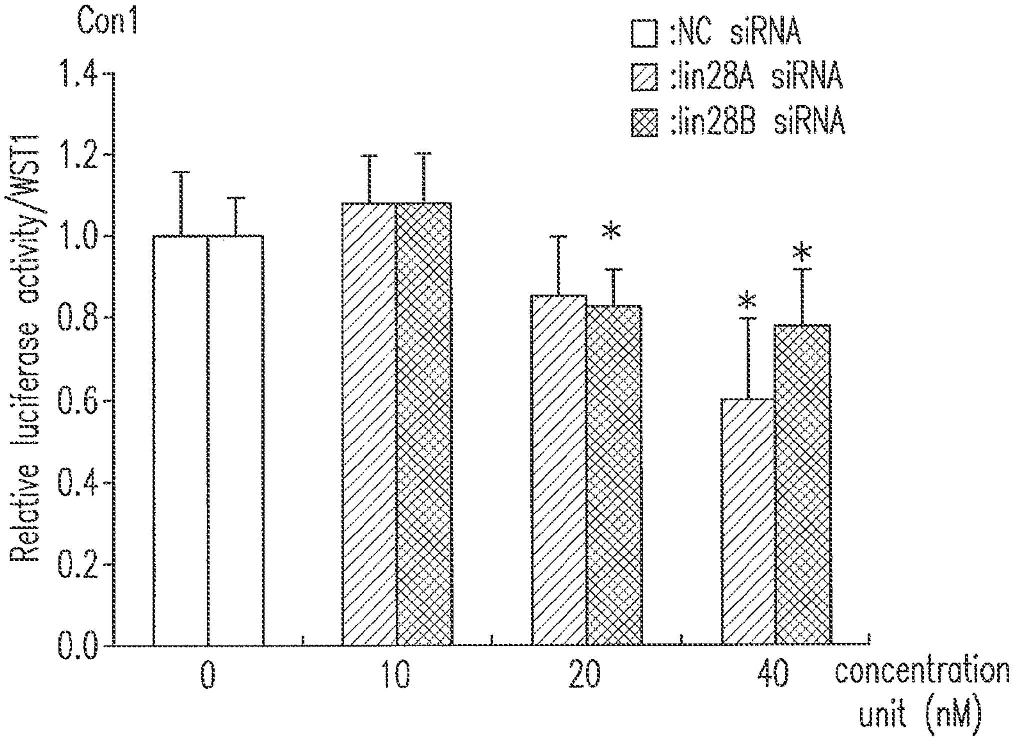
Figure 5F:
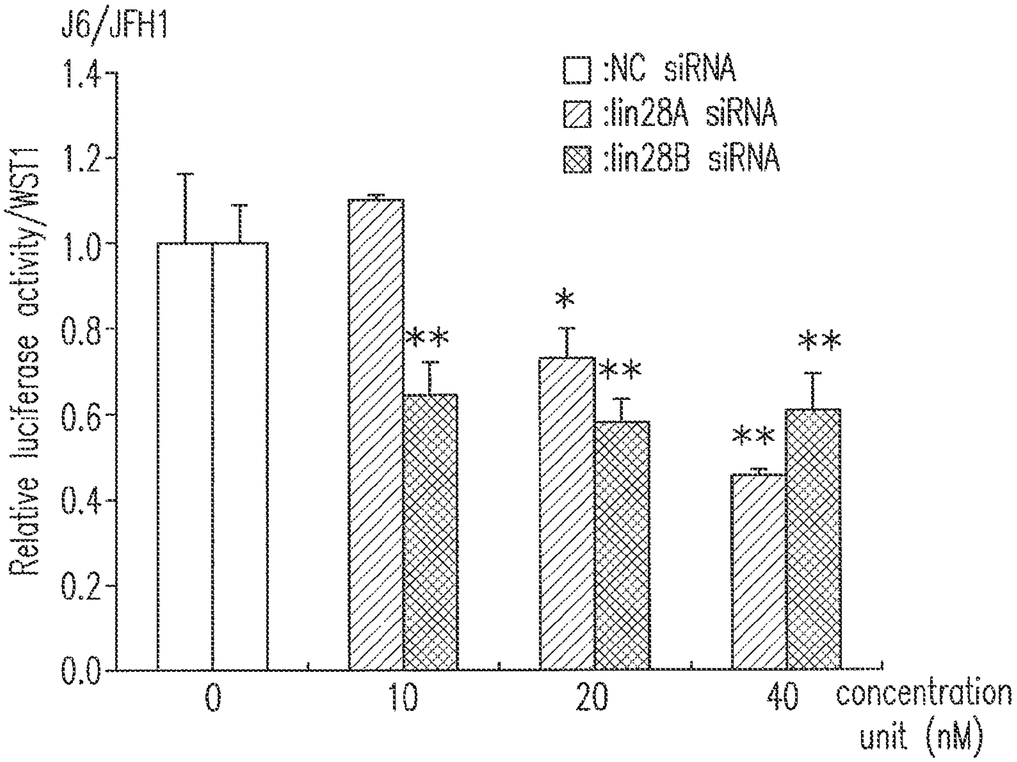

In FIG. 5(E), a lin28A siRNA, a lin28B siRNA or a negative control (NC) siRNA was transfected to a control group of Con1 cells. In FIG. 5(F), a lin28A siRNA, a lin28B siRNA or a NC siRNA was transfected to a J6/JFH cell line. 48 hours after the transfection, a luciferase activity test was performed, while a cell proliferation assay kit (WST1) served as an internal control, and the horizontal axis represents the concentration unit (nM). The data in this embodiment was sampled from three trials represented as the average±standard deviation with $^*P<0.05$, $^{**}P<0.005$.

Figure 5G:
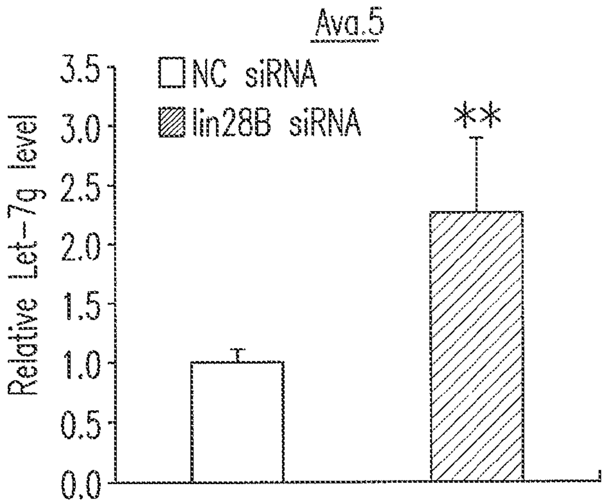

In FIG. 5(G), a lin28B siRNA or a NC siRNA was transfected to a Ava.5 cell line. 48 hours after the transfection, the relative level of the Let-7g was determined. The data was sampled from three trials represented as the average±standard deviation with $^{**}P<0.005$.

Figure 5H:
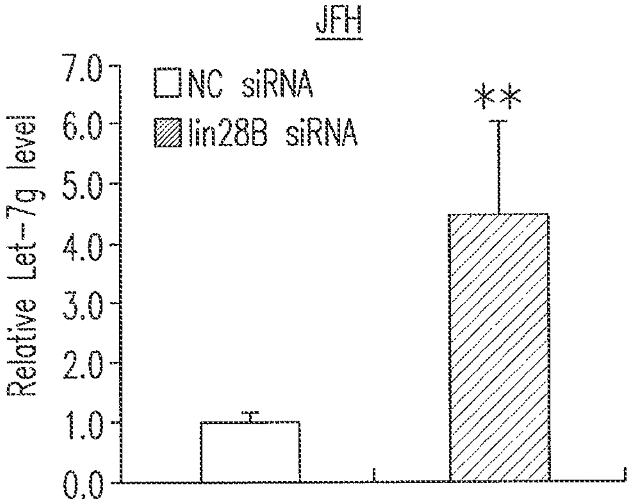

In FIG. 5(H), a lin28B siRNA or a NC siRNA was transfected to a cell line JFH. 48 hours after the transfection, the relative level of the Let-7g was determined. The data was sampled from three trials represented as the average±standard deviation with $^{**}P<0.005$.

The experimental results show that compared to the Huh7 cell line, expression levels of RNA-binding protein lin28A and lin28B in the Ava.5 cell line were lower (please refer to FIGS. 5(A)-5(B)).

Compared to the cell lines infected with the JFH1, expression levels of RNA-binding protein lin28A and lin28B in the Huh7.5.1 cell line were lower (please refer to FIGS. 5(C)-5(D)).

Compared to the control group, the luciferase activity in Con1 cells transfected with the lin28 siRNA basically decreased along with the concentration of the siRNA (please refer to the lin28A siRNA and the lin28B siRNA in FIG. 5(E)).

Compared to the NC siRNA, the luciferase activity in the J6/JFH1 cell line transfected with the lin28 siRNA basically decreased along with the concentration of the siRNA (please refer to FIG. 5(F)).

Compared to the NC siRNA, the relative level of the Let-7g in the Ava.5 cell line transfected with the lin28 siRNA was higher (please refer to FIG. 5(G)).

Compared to the NC siRNA, the relative level of the Let-7g in the cell line JFH transfected with the lin28 siRNA was higher (please refer to FIG. 5(H)).

As a result, one may deduce that the purpose of the RNA-binding protein lin28 is to regulate the expression level of a miRNA Let-7g in a replicon or a specimen infected with HCV. Moreover, a small interfering RNA for lin28 may up regulate the expression level of the miRNA Let-7g to down regulate the activity of the HCV.

Embodiment 8

Figure 6:
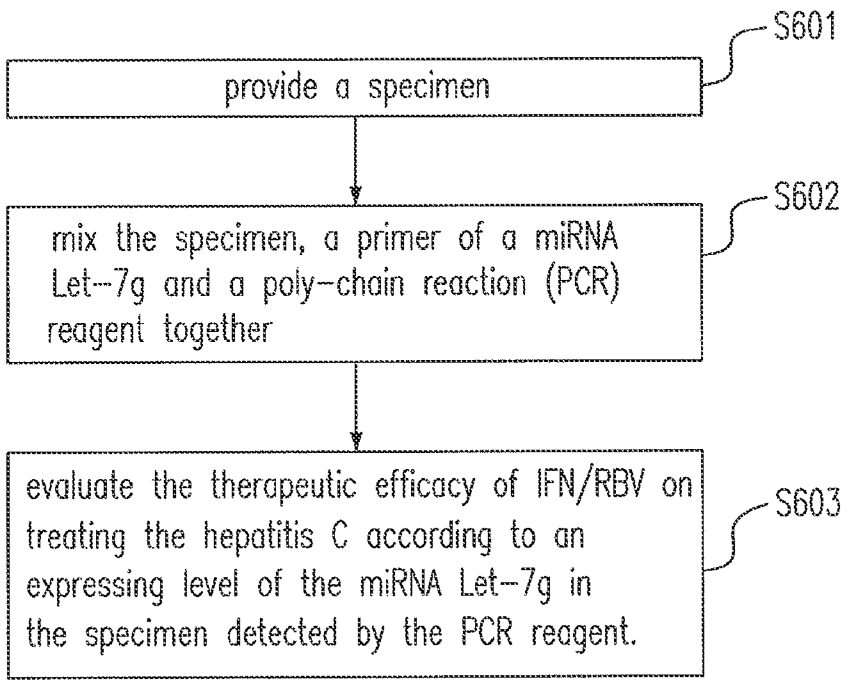
FIG. 6 shows a method for evaluating the therapeutic efficacy of interferon/ribavirin for hepatitis C in advance according to an embodiment of the present invention.

Please refer to FIG. 6, which shows a method for evaluating the therapeutic efficacy of interferon/ribavirin for hepatitis C in advance according to an embodiment of the present invention. The method includes the steps of providing a specimen, which may be sampled from cultured cells in vivo or in vitro (step S601); mixing the specimen, a primer of a miRNA Let-7g and a poly-chain reaction (PCR) reagent together (step S602); and evaluating the therapeutic efficacy of IFN/RBV to treat hepatitis C according to an expressing level of the miRNA Let-7g in the specimen detected by the PCR reagent (step S603).

Embodiment 9

Figure 7:
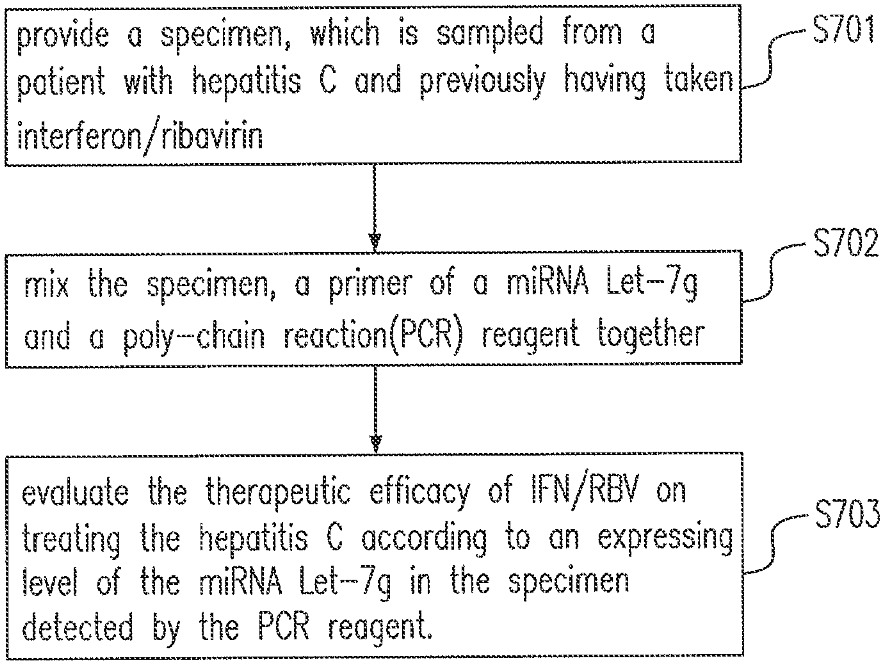
FIG. 7 shows a method for evaluating the therapeutic efficacy of interferon/ribavirin for hepatitis C according to an embodiment of the present invention.

Please refer to FIG. 7, which shows a method for evaluating the therapeutic efficacy of interferon/ribavirin for hepatitis C according to an embodiment of the present invention. The method includes the steps of providing a specimen, which is sampled from a patient with hepatitis C and previously having taken interferon/ribavirin (step S701); mixing the specimen, a primer of a miRNA Let-7g and a poly-chain reaction (PCR) reagent together (step S702); and evaluating the therapeutic efficacy of IFN/RBV to treat hepatitis C according to an expressing level of the miRNA Let-7g in the specimen detected by the PCR reagent (step S703).

The conditions and settings for the experiments of the present invention are described as follows.

[Material and Method]

All cell culture related reagents were purchased from GIBCO-BRL. Interferon IFNα-2a (ROFERON®-A) was purchased from Roche Corporation. All chemical reagents and ribavirin were purchased from Sigma-Aldrich Corporation. The enhanced chemiluminescence (ECL) solution was purchased from Millipore Corporation. The TRIZOL® reagent cartridge was purchased from Invitrogen Corporation. The luciferase detecting system was purchased from Promega Corporation. Pairs of Primers were purchased from Genomics Biotech Corporation (Taipei, Taiwan).

[Cell Culture]

Huh7 and Huh7.5.1 cell lines of Hepatocellular carcinoma, as well as Ava.5 cell line (type 1b) carrying a genome of the HCV were donated from Apath Corporation (St. Louis, Mo.). The cell lines were cultured in DMEM culture fluid containing 10% fetal bovine serum, 5% antibiotics and 5% non-essential amino acids. 1 mg/mL aminoglycoside antibiotics (G418) was further added in the Ava.5 cell line.

[In Vitro HCV Infection]

A cDNA of the JFH1 was donated from Dr. Takaji Wakita, National Institute of Infectious Diseases, Tokyo, Japan. And in vitro HCV infection was performed as follows: Huh7.5.1 cells were inoculated with concentrated JFH1 medium in a titer equivalent to $10^5$ HCV RNA copies. After 6 hours, the cells were washed three times with phosphate buffered saline and then maintained in a growth medium.

[miRNA Transfection]

The mirVana™ Let-7g mimic and the negative control were all purchased from Ambion Corporation®. The miRNA was transfected to cells using the Oligofectamine™ transfection reagent, which was purchased from Life Technologies Corporation.

[Construction of Plasmids for Hepatitis C Virus 5'UTR]

The plasmids for hepatitis C virus 5'UTR-WT and hepatitis C virus 5'UTR-DEL were synthesized by GENEWIZ Corporation (South Plainfield, N.J., USA).

[Apply Quantitative Real Time Polymerase Chain Reaction to Detect miRNA]

Detection of the Let-7g was performed using a TaqMan MicroRNA Reverse Transcription Kit for cDNA synthesis.

The Let-7g expression was determined using a Gene Amp 7900® Sequence Detection System machine (Applied Biosystems). The expression level of Let-7g in each sample was calibrated to the corresponding level of snU6B or RNU44.

[Western Blot]

Western Blot was used to assess the expression of the described proteins. The anti-core antibody was purchased from Thermo Scientific Corporation. The anti-NS5B antibody was purchased from ViroStat Corporation. The anti-GAPDH antibody was purchased from Millipore Corporation.

[Determination of HCV Titers in Supernatants]

The viral load of the HCV in supernatants was measured using the Abbott mSample Preparation System reagent M2000 instrument (Abbott, North Chicago, Ill.). The usage protocol followed the manufacturer's specifications.

[Separation of RNA and Quantitative Real Time Polymerase Chain Reaction]

Total RNA extraction was carried out using TRIzol® according to the manufacturer's instructions. The RNA quality was confirmed using A260/A280 readings. The cDNA was synthesized from 100 ng total RNA using a High Capacity cDNA Reverse Transcription Kit (Applied Biosystems, CA, USA). PCRs were performed using SYBR® Green PCR Master Mix (Applied Biosystems) on an ABI Prism 7900 sequence detection system. All the primers used can be seen in the following Table 4.

TABLE 4

| Primer name | Sequence |
|---|---|
| HCV NS5B | S: 5'-GGAAACCAAGCTGCCCATCA-3' (SEQ ID NO: 1)<br>AS: 5'-CCTCCACGGATAGAAGTTTA-3' (SEQ ID NO: 6) |
| HCV 5'UTR | S: 5'-TGCCTGGAGATTTGGGCGTGC-3' (SEQ ID NO: 2)<br>AS:5'-CAAGCACCCTATCAGGCAGT-3' (SEQ ID NO: 7) |
| MxA | S: 5'-GGTGGTGGTCCCCAGTAATG-3' (SEQ ID NO: 3)<br>AS: 5-ACCACGTCCACAACCTTGTCT-3' (SEQ ID NO: 8) |
| PKR | S: 5'-TCTCAGCAGATACATCAGAGATAAATTCT-3' (SEQ ID NO: 4)<br>AS: 5-AGTATACTTTGTTTCTTTCATGTCAGGAA-3' (SEQ ID NO: 9) |
| 2'5'-OAS | S: 5'-AAGAGCCTCATCCGCCTAGTC-3' (SEQ ID NO: 5)<br>AS: 5-AAATCCCTGGGCTGTGTTGA-3' (SEQ ID NO: 10) |

[Experiments of Clinical Samples]

Clinical samples were obtained from 17 patients with chronic hepatitis C (CHC) and 17 patients with non-alcoholic fatty liver disease (NAFLD) as controls. All of the CHC patients were biopsy-proven and treated with 24 or 48 weeks of PEG-IFN/ribavirin according to a corresponding viral genotype, and maintained at least 80% of the assigned treatment duration and regimen, including 11 patients achieving an SVR (RNA of the HCV that was undetectable for 24 weeks after the end of treatment) and 6 patients achieving non-SVR, the cases excepted from the definition of SVR. All of the NAFLD patients were seronegative for anti-HCV antibodies and HCV RNA. The protocols involved in human subjects were approved by the ethics committee at Kaohsiung Medical University Hospital, and were carried out under the guidelines of the International Conference on Harmonization for Good Clinical Practice. All participants gave their informed consent.

[Statistics]

Data for the continuous variables were expressed as the mean+standard deviation (SD). Paired t-tests were used to compare the difference between two groups. Student's t-test and $X^2$ were used to analyze the patient characteristics. A multivariate logistic regression model was used to determine the factors associated with the results. All p values are two-sided and less than 0.05, and were considered statistically significant. All statistical calculations were performed using the JMP software version 9.

To predict the complementarity between Let-7g and a genome of the hepatitis C virus, Miranda was used in the present invention to calculate and predict whether the Let-7g combined with the sequence of the genome of the hepatitis C virus. In most genotypes of the hepatitis C virus, the Let-7g was predicted to be capable of being combined with a 5'untranslated region (5'UTR) of the genome of the hepatitis C virus. Table 5 shows the possibility that the Let-7g may be combined with a 5'UTR of a different genotype of the hepatitis C virus.

TABLE 5

| Viral Genotype | Name | Gene Bank No. |
|---|---|---|
| 1a | D7 | DQ155448 |
| | DH092 | EU081312 |
| | 4025q | EU362903 |
| | DD070077 | DD070077 |
| | K-0374C | D31601 |
| 2/5 | recombinant-2/5 | AM408911 |
| 2a/1a | J6/JFH1(H77C-NS5A) | HQ852458 |
| 4a/2a | ED43-JFH1 | JF343785 |
| 4n | QC97 | FJ462441 |
| 6u | DH014 | EU408331 |
| 6u | DH110 | EU081306 |
| 6k | VN405 | D88468 |
| 6m | C-0208 | DQ835763 |
| 6b | Th580 | D37841 |
| 1b | 1B-5 | AB442222 |
| | K4preS-10 | AB492210 |
| | EP1043399-2 patent | AX036253 |
| | patient-1 | AY576587 |
| | JP1995133291-A/1 patent | E09288 |
| | HCVT191 | AB049096 |
| | DD448666 | DD448666 |
| | MD15 | AF207756 |
| | K4preS-18 | AB492211 |
| | patient-5 | AY576555 |
| | patient-4 | AY576558 |
| | D71 | DQ155485 |
| | HCVT221 | AB049101 |
| | HCV5UTRMG01 | EU360315 |
| | HC-J4 | D00832 |
| | HC-C2 | D10934 |
| | HCV-K1-R2 | D50481 |
| | T5S-4 | AB492187 |
| | Source | AF313916 |
| | D50 | DQ155473 |
| | Con12-I377/NS2-3'UTR | AJ242651 |
| | WO02052015-24 patent | AX472314 |
| | plasma-X | DQ319979 |
| | MD22 | AF207763 |
| | patient-8 | AY576568 |
| | patient-8 | AY576570 |
| | patient-6 | AY576600 |

In conclusion, the experimental data indicate that non-coding microRNA Let-7g is correlated to the infection of the hepatitis C virus, and provides another new targeted therapy against hepatitis C. However, further work will be required to further regulate the activity of a Let-7g, i.e. determining whether there is a transcriptional core region in a Let-7g promoter.

Embodiments

1. A method for evaluating a therapeutic efficacy of interferon (IFN)/ribavirin (RBV) for hepatitis C, comprising the steps of providing a specimen; mixing the specimen, a primer of a miRNA Let-7g and a poly-chain reaction (PCR) reagent altogether; and evaluating an efficacy of IFN/RBV on inhibiting a hepatitis C virus according to an expressing level of the miRNA Let-7g in the specimen detected using the PCR reagent.
2. The method of Embodiment 1, wherein the primer is a pair of primers.
3. The method of any one of Embodiments 1-2, further comprising a step of regulating the expressing level of the miRNA Let-7g in the specimen using an RNA-binding protein lin28.
4. The method of any one of Embodiments 1-3, wherein a small interfering RNA for lin28 (lin28 siRNA) up regulates the expressing level of the miRNA Let-7g, and thus down regulates an activity of the HCV.
5. A kit for evaluating a therapeutic efficacy of interferon (IFN)/ribavirin (RBV) for hepatitis C, comprising a primer of a miRNA Let-7g for mixing with a specimen; and a poly-chain reaction reagent for mixing with the primers of the miRNA Let-7g and the specimen, wherein the therapeutic efficacy of IFN/RBV is evaluated according to an expressing level of the miRNA Let-7g.
6. A method for regulating an activity of a hepatitis C virus (HCV), comprising a step of down regulating at least one of an expressing level of a NS5B gene, an expressing level of a core protein and a viral load of HCV using a miRNA Let-7g.
7. The method of Embodiment 6, wherein the miRNA Let-7g combines with nucleotides of No. 43-65 in 5'untranslated region (5'UTR) of a genome of the HCV.
8. The method of any one of Embodiments 6-7, further comprising a step of up regulating an expression of interferon-stimulated genes (ISGs) using the miRNA Let-7g.
9. The method of any one of Embodiments 6-8, wherein the HCV is sampled from a replicon in vitro
10. The method of any one of Embodiments 6-9, wherein the HCV is sampled from an infected cell in vitro 11. The method of any one of Embodiments 6-10, further comprising a step of using interferon/ribavirin additively to down regulate the activity of the HCV.
12. The method of any one of Embodiments 6-11, further comprising a step of regulating an expressing level of the miRNA Let-7g in a cell by an RNA-binding protein lin28.
13. The method of any one of Embodiments 6-12, wherein the ISGs includes 2'-5' oligoadenylate synthetase (OAS).
14. The method of any one of Embodiments 6-13, wherein the ISGs includes myxovirus resistance protein A (MxA).
15. The method of any one of Embodiments 6-14, wherein the cell includes a replicon.
16. The method of any one of Embodiments 6-15, wherein the cell is infected with the HCV.
17. The method of any one of Embodiments 6-16, wherein a small interfering RNA for lin28 (lin28 siRNA) up regulates the expressing level of the miRNA Let-7g, and thus down regulates the activity of the HCV.

Let-7g While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims which are to be accorded with the broadest interpretation so as to encompass all such modifications and similar structures.

SEQUENCE LISTINGS

<110> Kaohsiung Medical University
<120> THE USE OF LET-7G TO DOWN REGULATE NS5B GENE, CORE PROTEIN AND VIRAL LOAD OF HEPATITIS C VIRUS
<211> 20
<212> DNA
<213> HCV
<223> HCV NS5B primer
<400> 1
GGAAACCAAG CTGCCCATCA 20
<110> Kaohsiung Medical University
<120> THE USE OF LET-7G TO DOWN REGULATE NS5B GENE, CORE PROTEIN AND VIRAL LOAD OF HEPATITIS C VIRUS
<211> 21
<212> DNA
<213> HCV
<223> HCV 5'UTR primer
<400> 1
TGCCTGGAGA TTTGGGCGTGC 21
<110> Kaohsiung Medical University
<120> THE USE OF LET-7G TO DOWN REGULATE NS5B GENE, CORE PROTEIN AND VIRAL LOAD OF HEPATITIS C VIRUS
<211> 20
<212> DNA
<223> MxA primer
<400> 1
GGTGGTGGTC CCCAGTAATG 20
<110> Kaohsiung Medical University
<120> THE USE OF LET-7G TO DOWN REGULATE NS5B GENE,
CORE PROTEIN AND VIRAL LOAD OF HEPATITIS C VIRUS
<211> 29
<212> DNA
<223> PKR primer
<400> 1
TCTCAGCAGA TACATCAGAG ATAAATTCT 29
<110> Kaohsiung Medical University
<120> THE USE OF LET-7G TO DOWN REGULATE NS5B GENE, CORE PROTEIN AND VIRAL LOAD OF HEPATITIS C VIRUS
<211> 21
<212> DNA
<223> 2'5'-OAS primer
<400> 1
AAGAGCCTCA TCCGCCTAGTC 21

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
```

-continued

```
<223> OTHER INFORMATION: HCV NS5B primer

<400> SEQUENCE: 1

ggaaaccaag ctgcccatca                                                20


<210> SEQ ID NO 2
<211> LENGTH: 21
<212> TYPE: DNA
<213> ORGANISM: Artificial Sequence
<220> FEATURE:
<223> OTHER INFORMATION: HCV 5'UTR primer

<400> SEQUENCE: 2

tgcctggaga tttgggcgtg c                                              21


<210> SEQ ID NO 3
<211> LENGTH: 20
<212> TYPE: DNA
<213> ORGANISM: Artificial Sequence
<220> FEATURE:
<223> OTHER INFORMATION: MxA primer

<400> SEQUENCE: 3

ggtggtggtc cccagtaatg                                                20


<210> SEQ ID NO 4
<211> LENGTH: 29
<212> TYPE: DNA
<213> ORGANISM: Artificial Sequence
<220> FEATURE:
<223> OTHER INFORMATION: PKR primer

<400> SEQUENCE: 4

tctcagcaga tacatcagag ataaattct                                      29


<210> SEQ ID NO 5
<211> LENGTH: 21
<212> TYPE: DNA
<213> ORGANISM: Artificial Sequence
<220> FEATURE:
<223> OTHER INFORMATION: 2'5'-OAS primer

<400> SEQUENCE: 5

aagagcctca tccgcctagt c                                              21


<210> SEQ ID NO 6
<211> LENGTH: 20
<212> TYPE: DNA
<213> ORGANISM: Artificial Sequence
<220> FEATURE:
<223> OTHER INFORMATION: HCV NS5B primer

<400> SEQUENCE: 6

cctccacgga tagaagttta                                                20


<210> SEQ ID NO 7
<211> LENGTH: 20
<212> TYPE: DNA
<213> ORGANISM: Artificial Sequence
<220> FEATURE:
<223> OTHER INFORMATION: HCV 5'UTR primer

<400> SEQUENCE: 7

caagcaccct atcaggcagt                                                20
```

-continued

```
<210> SEQ ID NO 8
<211> LENGTH: 21
<212> TYPE: DNA
<213> ORGANISM: Artificial Sequence
<220> FEATURE:
<223> OTHER INFORMATION: MxA primer

<400> SEQUENCE: 8

accacgtcca caaccttgtc t                                              21


<210> SEQ ID NO 9
<211> LENGTH: 29
<212> TYPE: DNA
<213> ORGANISM: Artificial Sequence
<220> FEATURE:
<223> OTHER INFORMATION: PKR primer

<400> SEQUENCE: 9

agtatacttt gtttctttca tgtcaggaa                                      29


<210> SEQ ID NO 10
<211> LENGTH: 20
<212> TYPE: DNA
<213> ORGANISM: Artificial Sequence
<220> FEATURE:
<223> OTHER INFORMATION: 2'5'-OAS primer

<400> SEQUENCE: 10

aaatccctgg gctgtgttga                                                20
```

What is claimed is:

1. A method for treating hepatitis C of a patient according to evaluating a therapeutic efficacy of interferon (IFN)/ribavirin (RBV) on inhibiting a hepatitis C virus, comprising the steps of:

providing a specimen of the patient containing a microRNA Let-7g (miRNA Let-7g);

mixing the specimen containing the miRNA Let-7g, a primer of the miRNA Let-7g and a polymerase chain reaction (PCR) reagent altogether;

performing a quantitative real time PCR on the miRNA Let-7g using the primer and the PCR reagent to obtain a CT(Let-7g) value:

evaluating the therapeutic efficacy of IFN/RBV on inhibiting the hepatitis C virus according to an expressing level of the miRNA Let-7g in the specimen, wherein the expressing level of miRNA Let-7g is represented by LOG $10(2^{-\Delta CT})$, $\Delta CT=CT(Let\text{-}7g)-CT$ (an internal control), and when the expressing level of the miRNA Let-7g is more than 1.14 the therapeutic efficacy of IFN/RBV on inhibiting the hepatitis C virus in the specimen is confirmed; and administering an effective amount of IFN/RBV to the patient that the therapeutic efficacy of IFN/RBV on inhibiting the hepatitis C virus is confirmed.

2. The method as claimed in claim 1, wherein the primer is a pair of primers.

3. The method as claimed in claim 1, wherein the internal control is snU6B.

* * * * *